United States Patent [19]

Falholt et al.

[11] Patent Number: 4,906,396

[45] Date of Patent: Mar. 6, 1990

[54] PROTECTED ENZYME SYSTEMS

[75] Inventors: Per Falholt, Gentofte; Arne D. Fog, Birkeroed, both of Denmark; Anthony Martin, Cumbria, England

[73] Assignees: Albright & Wilson limited, Warley, United Kingdom; Novo-Nordisk A/S, Bagsvaerd, Denmark

[21] Appl. No.: 16,874

[22] Filed: Feb. 20, 1987

[30] Foreign Application Priority Data

| | | | |
|---|---|---|---|
| Feb. 20, 1986 | [GB] | United Kingdom | 8604164 |
| Jul. 2, 1986 | [GB] | United Kingdom | 8616137 |

[51] Int. Cl.[4] .......... C11D 3/386; C12N 9/96

[52] U.S. Cl. .......... 252/174.12; 252/90; 252/92; 252/174.13; 252/DIG. 12; 435/188

[58] Field of Search .......... 435/188; 252/174.12, 252/174.13, DIG. 12, 90, 92

[56] References Cited

U.S. PATENT DOCUMENTS

| | | | |
|---|---|---|---|
| 2,642,376 | 6/1953 | Gale et al. | 435/188 |
| 4,115,292 | 9/1978 | Richardson et al. | 252/174.12 |

FOREIGN PATENT DOCUMENTS

| | | |
|---|---|---|
| 6638 | 1/1980 | European Pat. Off. . |
| 130064 | 1/1985 | European Pat. Off. . |
| 2123846 | 2/1984 | United Kingdom . |
| 2153380 | 8/1985 | United Kingdom . |

*Primary Examiner*—Robert A. Wax

*Attorney, Agent, or Firm*—Frishauf, Holtz, Goodman & Woodward

[57] ABSTRACT

A protected enzyme system suitable for storage, prior to use, in a medium such as a liquid detergent which causes degradation of the unprotected enzyme, which system comprises at least one enzyme dispersed in a hydrophobic substance which does not dissolve on storage and which is liquid under the conditions of use.

19 Claims, No Drawings

PROTECTED ENZYME SYSTEMS

The present invention relates to protected enzyme systems which are suitable for storage or use in environments which tend to cause degradation of enzymes, such as liquid laundry detergents.

Enzymes are commonly employed as stain removing agents in powder detergents but their incorporation in liquid cleaning preparations including liquid laundry detergents, such as those described for example in GB 2123846 and GB 2153380 has hitherto presented serious problems. Those liquid formulations which are most effective for soil removal cause rapid degradation of washing enzymes, often resulting in significant loss of stain removing properties after only a few days of storage. The relatively high alkalinity of the more effective soil removing formulations and the chemical action of most of the builder systems and surfactants present therein are particularly antagonistic to detergent enzymes and have largely prevented their use in such detergents but serious deterioration is observed even in comparatively non-alkaline compositions, which have been specially formulated to permit incorporation of enzymes. Even in powder detergents some degradation of enzymes may be observed, especially if the powder is highly alkaline as in mechanical dishwashing powders, or contains an oxidising bleach such as perborate.

We have now discovered that the deterioration of enzymes in hostile environments such as liquid detergents is substantially reduced when the enzymes are dispersed in a hydrophobic material provided that the latter is insoluble in the particular environment. We have discovered, moreover, that the protected enzyme is available to perform its normal function provided that the hydrophobic material is sufficiently fluid or friable to be disrupted under the conditions of use.

According to one embodiment, therefore, our invention provides a protected enzyme system for storage prior to use, in an environment which causes progressive degradation of unprotected enzymes said system consisting essentially of a dispersion of at least one enzyme in a hydrophobic substance which is insoluble in the said environment, and which is sufficiently fluid or friable to be disrupted under the normal conditions of use.

According to a preferred aspect our invention provides a protected enzyme system for use in a liquid cleaning composition said system comprising at least one detergent enzyme dispersed in a hydrophobic substance which is insoluble in the liquid detergent but dispersible therein as particles or droplets, and which is sufficiently fluid or friable to be disrupted under cleaning conditions.

According to a second embodiment our invention provides a protected enzyme system for use in a liquid cleaning composition consisting essentially of granules comprising at least one detergent enzyme encapsulated within a hydrophobic substance which is not soluble in the liquid cleaning composition and which is fluid or friable at normal wash temperatures.

According to a third embodiment our invention provides a protected enzyme system for use in liquid detergent compositions consisting essentially of a dispersion of a detergent enzyme in a hydrophobic liquid which is insoluble in liquid detergent.

According to a fourth embodiment our invention provides a method of protecting an enzyme for storage prior to use in an environment which tends to cause progressive degradation of unprotected enzymes, which method comprises dispersing the enzyme in a hydrophobic medium which is insoluble in said environment but dispersible therein as particles or droplets and which is fluid or friable under the normal conditions of use.

According to a fifth embodiment our invention provides a method of protecting enzymes which comprises dispersing a detergent enzyme in a hydrophobic substance which is insoluble in liquid detergent, and fluid at normal wash temperatures.

According to a sixth embodiment our invention provides a liquid cleaning composition having dispersed therein particles or droplets of a protected enzyme system of our invention as hereinbefore described.

References herein to solubility in a medium refer to both dissolution in an aqueous or other continuous solvent phase of the medium and solubilisation in surfactant micelles or any other discontinuous phase dispersed in the medium.

The hydrophobic material may be an organo polysiloxane oil, e.g. a poly di(alkyl)siloxane, wherein the alkyl group has preferably from 1 to 4 carbon atoms, especially a poly di(methyl)siloxane. Especially preferred are hydrophobic liquids which have been stabilised by suspending therein hydrophobic solid particles. Examples include the silicone compositions which have been proposed for use as antifoam in liquid detergents which comprise hydrophobic silicone oil and hydrophobic silica, e.g. a finely divided silica with a silicone at least partly bonded to the surface of the silica particles. For example a hydroxy functional organosiloxane may be condensed with the hydroxy groups of the silica surface. Examples of such compositions include those sold under the Registered Trade Marks "WACKER" Antifoam S132, "BEVALOID" 4237, "UNION CARBIDE" Y1206, or DIAMOND SHAMROCK'S "NOPCO" 8315. The silicone antifoam may be diluted with an unmodified silicone oil such as a poly dimethyl siloxane. Furthermore the viscosity of the silicone may be increased by addition of finely divided silica eg, fumed silica such as Degussa's "AEROSIL" 200 (RTM)

Alternatively the hydrophobic material may be a high molecular weight hydrocarbon, e.g. petroleum bright stock or a so-called petroleum jelly, a high molecular weight alcohol, e.g. more than 28 carbon atoms or a high molecular weight fluocarbon or a hydrophobic phosphate ester such as a mono- and/or di-fatty alkyl phosphate ester or a salt thereof especially a sodium or calcium salt or a trialkyl or triaryl phosphate. Hydrophobic fluid materials may be further stabilised by inclusion of hydrophobic solid particles, e g. those formed by condensing silica with silicone as described above or with a fatty alcohol. According to one embodiment the hydrophobic material may be a solid or waxy material at ambient temperature, which has a softening or preferably melting point below normal wash temperature, e.g. below 60° C., preferably below 50° C., more usually 40° C., often below 30° C. Such solid materials provide products which are particularly suitable for use in powder as well as liquid detergents. Typically we prefer that our hydrophobic material has a viscosity greater than 0.05 Pascal seconds at normal storage temperature (e.g. room temperature) preferably greater than 0.2, more preferably greater than 0.5 and most preferably greater than 0.8 Pascal seconds. In particular we prefer that the viscosity should be greater than 1 Pascal second e.g. greater than 2 Pascal seconds, especially greater than 10 Pascal seconds. We prefer that the viscosity should be les than 200 Pascal seconds, most preferably less than 100 Pascal seconds, e.g. less than 60 Pascal seconds and especially less than 40 Pascal seconds, at the temperature of use. Fluid materials having a viscosity between 1 and 50 Pascal seconds at ambient temperature are especially suitable.

Unless stated to the contrary, all references herein to viscosities are as measured at 24 $sec^{-1}$ shear and at 25° C.

The enzyme may for example be a detergent enzyme, such as a protease, lipase, amylase, decarboxylase, or cellulase, such as those sold by Novo Industri AS under the Registered Trade Marks "SAVINASE", "TERMANYL", "ESPERASE" and "ALCALASE", or other enzymes which are active in the removal or amelioration of soil or stains or a mixture of such enzymes.

The enzyme may be present in the hydrophobic material in the form of dispersed droplets of a solution of enzyme, e.g. in water or a lower, preferably water miscible, mono-, di- or polyhydric alcohol such as propylene glycol and optionally containing an enzyme stabiliser such as is known in the art. Enzyme stabilisers which may be present include lower alcohols, e.g. glycerol, lower mono- or di-carboxylic acids and their salts, especially formates and oxalates, borates and calcium salts.

Alternatively the enzyme may be present in the form of suspended particles of an enyzme-containing solid, the solid enzyme being preferably obtained by drying or precipitation from an enzyme solution, optionally containing a stabiliser as aforesaid, e.g. as described in U.S. Pat. No. 3,723,250, particularly at column 12; EP 0 006 638, Example 2a and b GB 1,296,839 U.S. Pat. No. 4,435,307; EP 0 130 064 or Belgian Patent 889336.

The enzyme may also be present in a water soluble granule or marume. Typically this is the form in which enzymes are sold commercially. Thus a soluble crystalline carbohydrate such as sucrose or a salt such as sodium chloride, sodium carbonate or sodium sulphate may be granulated or marumerised with the enzyme, and, optionally, with enzyme stabilisers, e.g. as described in U.S. Pat. No. 4106,991 or GB 1,362,365, page 9, and the product dispersed in, or coated with, silicone or a hydrocarbon, such as petroleum jelly.

The enzyme may be incorporated in the inert oil by dispersion by simple stirring. Where the hydrophobic material is solid at room temperature it may first be melted before dispersing the enzymes and subsequently cooled to room temperature. Optionally the dispersion may be spray cooled to provide a particulate product.

The proportion of enzyme in the protected enzyme system may be determined by the desired viscosity of the system, where it is desired to handle or store the latter as a liquid. Higher proportions tend to provide higher viscosities, but are less prone to sedimentation of the dispersed enzyme. However, we do not exclude the use of sedimenting systems provided that the enzymes can be easily redispersed by stirring before the system is added to the detergent composition.

Preferably the particle size and proportion of the enzyme are chosen to provide an overall viscosity of the protected system greater than 0.1 Pascal seconds, typically greater than 0.5 Pascal seconds especially greater than 1 Pascal second more preferably greater than 2 Pascal seconds, e.g. greater than 3 Pascal seconds and optionally greater than 10 Pascal seconds, under the conditions of storage and less than 200 Pascal seconds, more preferably less than 100 Pascal seconds, e.g. less than 70 Pascal seconds under the conditions of use. Systems having a viscosity in the range of 2 to 60 Pascal seconds at ambient temperature are generally preferred.

Where enzyme is incorporated in the system as a solution, the solution preferably contains 1 to 90% by weight of enzyme concentrate, e.g. 2 to 80%, typically 5 to 60%, and its dispersion in the oil typically contains 1–80, more usually 5–70, preferably 10–60, more preferably 15–50, e.g. 20–40 or 30–50% by weight of enzyme solution, the percentages being expressed by weight of the total protected enzyme system. The suspension of solid enzyme concentrate in the hydrophobic material typically contains 1 to 90, more usually 5 to 80, preferably 20–60, e.g. 30–50 or 20–30% by weight of solid, based on the total weight of suspension.

The proportion of enzyme in the protected enzyme system may depend on whether the hydrophobic substance is required to perform any useful function in its own right, e.g. as antifoam. Where a low foaming composition is required the enzyme and antifoam may conveniently be in the same relative proportions as those which are required in the final composition. Alternatively a more concentrated suspension of enzyme may be prepared and diluted with more antifoam prior to use, or added to the composition simultaneously with or separately from the additional antifoam.

Where the hydrophobic mateerial is not required to perform a useful function other than protecting enzyme, the enzyme concentration may be the maximum which is consistent with a manageable product.

The particle size of the dispersed enzyme in the protected enzyme system can vary within wide limits. Typically the dispersed enzyme may have a particle size in the range 1$\mu$ to 2 mm, preferably 5$\mu$ to 1 mm, e.g. 10$\mu$–700$\mu$. Solid enzyme concentrates tend to be in the lower part of the above range, liquid solutions are normally dispersed with a particle size in the middle of the range, e.g. 100$\mu$–800$\mu$. Granular enzymes usually have a particle size in the upper part of the range, e.g. 300$\mu$–1 mm.

The protected enzyme system is generally readily dispered in the liquid detergent by simple stirring. The system may be dispersed as particles or droplets of from 2$\mu$ to 2.5 mm diameter, more usually 5$\mu$–500$\mu$, preferably 10$\mu$–100$\mu$, where a dispersed solution or concentrate of enzyme is used as the protected system. Where the enzyme is present as a granulate, the preferred particle size of the system in the liquid detergent is 500$\mu$ to 1 mm.

Dispersants and emulsifiers may be used as required but are not usually preferred.

Preferably the composition is added to a liquid detergent which comprises an aqueous phase, surfactant, sufficient electrolyte dissolved in the aqueous phase to form with the surfactant, a structure capable of supporting suspended particles, and a protected enzyme system of our invention, suspended in the detergent composition.

Preferably the composition contains an effective amount of a detergent builder. Suitable builders include condensed phosphates, especially sodium tripolyphosphate or, less preferably, potassium pyrophosphate or sodium tetraphosphate, sodium carbonate, sodium silicate, sodium orthophosphate, sodium citrate, sodium nitrilotriacetate, a phosphonate such as sodium ethylenediamine tetramethylene phosphonate, sodium aceto diphosphonate or sodium aminotris(methylene phosphonate), sodium ethylenediamine tetracetate or a zeolite. Other less preferred builders include potassium or lithium analogues of the above sodium salts.

The proportion of builder is typically from about 5% to about 40% by weight of the liquid detergent composition, usually 10% to 35%, preferably 15%-30%, more preferably 18% to 28%, most preferably 20 to 27%. Mixtures of two or more builders are often employed, e.g. sodium tripolyphosphate with sodium silicate and/or sodium carbonate, or with zeolite, or sodium nitrilotriacetate with sodium citrate.

Preferably the builder is at least partly present as solid particles suspended in the composition.

Particularly preferred are liquid detergent compositions according to the aforesaid GB 2,123,846 or GB 2,153,380.

The invention is also applicable to the preparation of unbuilt cleaning compositions or compositions in which all the builder is present in solution.

The surfactant may be an anionic, nonionic, cationic, amphoteric, zwitterionic and/or semi polar surfactant which may typically be present in concentrations of from 2 to 35% by weight of the composition, preferably 5 to 30%, more usually 7 to 25%, e.g. 10 to 20%.

Usually the composition contains an alkyl benzene sulphonate together with one or more other surfactants such as an alkyl polyoxyalkylene sulphate and/or a non-ionic surfactant. The latter may typically be an alkanolamide or a polyoxyalkylated alcohol.

Other anionic surfactants include alkyl sulphate, alkane sulphonates, olefin sulphonate, fatty ester, sulphonates, soaps, alkyl sulphosuccinates, alkyl sulphosuccinamates, taurides isethionates and polyoxyalkylene derivatives of the aforesaid categories of anionic surfactant. In every case the surfactant for use herein has an alkyl group with an average of from 8 to 22 preferably 10 to 20, e.g. 12 to 18 carbon atoms. Alkyl groups are preferably primary and straight chain, however we do not exclude branched chain or secondary alkyl groups. In the case of alcohol based non-ionics the branched chain are sometimes preferred.

The surfactant may be wholly or predominantly nonionic, e.g. a polyoxyalkylated alcohol alone or in admixture with a polyoxyalkylene glycol. Other non-ionic surfactants which may be used include polyoxyalkylated derivatives of carboxylic acids, glycerol, sorbitan, alkylphenols, alkylolamides or amine oxides.

All references herein to polyoxyalkylene groups are preferably to polyoxyethylene groups, or less preferably to polyoxypropylene or mixed oxyethylene oxypropylene copolymeric or block copolymeric groups or to such groups with one or more glyceryl groups. Preferably the polyoxyalkylene groups have from 1 to 30, more usuallly 2 to 20, e.g. 5 to 15, alkyleneoxy units.

Cationic surfactants for use according to our invention include quaternised alkyl amines, amido amines and imidazolines. Amphoteric surfactants include betaines and sulphobetaines.

In general any surfactant referred to in GB 1,123,846, or in "Surface Active Agents and Detergents" by Schwartz, Perry and Berch, may be used.

Preferably the pH of the liquid detergent composition is alkaline, e.g. about 7.5, especially 7.5 to 12 typically 8 to 11, e.g. 9 to 10.5.

Preferably the liquid detergent composition contains dissolved electrolyte. This may comprise a dissolved portion of the builder and/or any other salt, inorganic or organic, which is not itself a surfactant and which salts out the surfactants present from solution (including micellar solution). Examples include sodium chloride, sodium nitrate, sodium bromide, sodium iodide, sodium borate, sodium formate, or sodium acetate, or corresponding potassium salts. Preferably, however, the electrolyte is a salt which is required to perform a useful function in the wash liquor.

The electrolyte may comprise sodium sulphate in minor concentrations, but electrolyte mixtures containing concentrations of sodium sulphate of about 3% or over based on the total weight of the detergent composition, are preferably not used because they give rise to undesirable crystallisation on standing.

The detergent composition may contain any of the usual minor ingredients such as soil suspending agents (e.g. carboxymethyl cellulose), optical brightening agent, perfume, colouring and, optionally, a bleach.

Particularly preferred liquid detergents are those containing long chain, e.g. $C_{10-14}$ linear alkyl benzene sulphonates in an amount of 5-12%, long chain alkyl ether sulphates, e.g. with 1-5 ethyleneoxy units in amount of 0-3%, fatty acid alkanolamides, e.g. diethanolamides in amount of 1-5%, mixtures of mono and di long chain alkyl phosphates in amount of 0-3%, e.g. 0.1-1%, sodium tripolyphosphate (preferably prehydrated with from 0.5 to 5% by weight of water) in an amount of 14-30;1 %, e.g. 14-18% or 20-30% and optionally sodium carbonate in an amount of up to 10%, e g. 5-10%, with the total of sodium tripolyphosphate and carbonate of 20-30%, antiredeposition agents such as sodium carboxymethyl cellulose in amount of 0.05-0.5%, optical brightening agent in amount of 0.05-0.5%, chelating agents, e.g. amino phosphonates such as methylene phosphonates of di and polyamines especially sodium ethylenediamine tetra[methylene phosphonate] or diethylene triamine hexa[methylene phosphonate] optionally present in amount of 0.1-1%, together with conventional additives such as perfume, the remainder being water, the percentages being by weight of the total liquid detergent. The liquid detergent may have a pH of 6 to 13, preferably 7 to 12, more usually 8 to 11, e.g. 9 to 10.5.

The compositions of the invention may typically contain 0.01 to 10%, e.g. 0.05-0.5% by weight of the protected enzyme system.

Our protected enzyme systems are useful as additives to powder cleaning compositions. For instance enzyme dispersed in silicone antifoam or viscous hydrocarbon may be incorported into a powder laundry detergent. Conventionally such powders may contain surfactant (usually in total amounts of from 5 to 30% by wt.). builder, a solid filler and optionally a bleach. Usually the surfactant comprises a sodium alkyl (preferably $C_{12-14}$ linear) benzene sulphonate in amounts of from 2 to 20%, preferably 5 to 15%, by weight of the total composition and optionally a sodium alkyl (e.g. $C_{12-18}$) polyoxyethylene (e.g. 2 to 10% mole) sulphate and/or a non-ionic surfactant such as an alkanolamide, e g. coconut, mono- or di-ethanolamide and/or a polyethoxylated fatty alcohol.

The builder is typically sodium tripolyphosphate although zeolites, sodium carbonate, sodium silicates, sodium citrate, sodium nitrilotriacetate and mixtures thereof may be present as well as or in place of sodium tripolyphosphate. The total amount of builder is usually between 10 and 40% by weight of the total powder, e.g. 20 to 30%.

The filler is typically sodium sulphate which may typically be present in a proportion of from 0 to 60;1% usually 20 to 50% of the total composition in order to ensure a free flowing powder.

The bleach is normally a peroxy compound especially a perborate or percarbonate.

The powder also usually contains the usual minor ingredients such as soil suspending agent (typically sodium carboxymethyl cellulose) optical brightening agent and perfume and optionally colouring.

Protected enzyme systems according to our invention may be added to machine dishwashing powders, scouring creams and other hard surface cleaners, carpet shampoos, degreasing compositions, oven cleaners, dishwashing liquids, soap powders, laundry pre soak compositions and other cleaning preparations.

Dishwashing powders according to our invention may typically comprise a substantial proportion, e.g. 20 to 60%, preferably 30 to 50%, of an alkali such as a sodium carbonate and a minor proportion, e.g. 1 to 5%, of surfactant preferably a non-ionic surfactant such as an alkoxylated alcohol, together, optionally but preferably, with a builder such as sodium tripolyphosphate in proportions of up to about 45% by weight of the composition, e.g. 20 to 35%, an alkaline silicate such as sodium metasilicate and an alkaline buffer such as borax. The composition may optionally contain a bleach such as chlorinated trisodium phosphate and from 0.1 to 2% by weight of the protected enzyme system.

Liquid dishwashing compositions of our invention typically comprise highly soluble builders such as potassium pyrophosphate, and/or potassium silicate in a total concentration of 10 to 30% by weight, surfactants, preferably non-ionic in concentrations of 0.2 to 5% by weight and hydrotropes such as sodium xylene sulphonate, sodium toluene sulphonate or sodium benzene sulphonate in concentrations of 1 to 10% by weight.

Hard surface cleaners of our invention may typically comprise 1 to 10%, surfactant, typically non-ionic or anionic/nonionic mixtures, 1 to 10% hydrotrope and 2 to 10% soluble builder such as potassium pyrophosphate. Hard surface cleaners may also optionally comprise abrasives such as silica, or calcium carbonate as arragonite or calcite suspended in a structural liquid.

Carpet shampoos according to our invention may according to our invention comprise relatively high concentrations, e.g. 5 to 20% by weight, of high foaming surfactant such as mixtures of anionic surfactants (e.g. alkyl sulphates) with foaming agents (e.g. alkanolamides).

Oven cleaners according to our invention may be of the caustic type comprising, e.g. 4 to 12% of alkalis such as sodium hydroxide, and typically a high foaming anionic surfactant such as a sodium alkyl ether sulphate, or else of the solvent based type containing e.g. 10 to 30% of a water miscible organic solvent such as a lower mon- di- or polyhydric alcohol or other alcohol, e.g. propylene glycol, and typically a non ionic surfactant, together preferably with a builder such as sodium tripolyphosphate.

Any difficulties in dispersing the protected enzyme system in any of the foregoing liquid formulations is generally avoided by addition of small amounts of conventional dispersants or suspending agents such as soluble gums or polyelectrolytes.

Normal wash conditions for laundry detergents involve temperatures of from 50° C. to 60° C. and a wash liquor containing about 2 to 15 gm per litre of detergent composition under vigorous agitation. Some detergents, however, are formulated and recommended for use at cool or intermediate wash temperatures (20 to 30 or 30° to 40° C. respectively), either for sensitive fabrics or energy saving.

The invention is illustrated by the following Examples.

EXAMPLE 1

A protease solution, sold under the Registered Trade Mark "Esperase" 8 OL, was dispersed in a mixture of equal parts by weight of an antifoam silicone oil having a viscosity of 22.57 Pascal seconds at 24 $sec^{-1}$ and 25° C. which contains a hydroxyl terminated polysiloxane condensed with solid fumed silica, and is sold under the Registered Trade Mark "Wacker" Antifoam S132 and a neutral polysiloxane oil, sold under the Registered Trade Mark "Wacker" AK50. The silicone mixture had a viscosity of 3.4 Pascal seconds. The dispersion produced contained 38% by weight of the enzyme solution, based on the total weight of dispersion and had a viscosity of 11.9 Pascal seconds at 24 $sec^{-1}$ and 25° C.

The dispersion was incorporated by thorough stirring into a liquid built detergent to give the following formulation:

| | wt. % |
|---|---|
| Sodium linear $C_{12}$ alkyl benzene sulphonate | 9.3 |
| Sodium linear $C_{12-18}$ alkyl ether sulphate containing an average of 3 ethyleneoxy units per molecule | 1.85 |
| Coconut diethanolamide | 1.85 |
| Sodium tripolyphosphate | 16.7 |
| Sodium carbonate | 6.7 |
| Sodium carboxymethyl cellulose | 0.9 |
| Optical brightening agent | 0.1 |
| Enzyme dispersion | 3 |
| pH | 10.5-11.0 |

This formulation was compared with the same formulation without enzyme as Control for stain removal from a test sample of cotton stained with blood, milk and carbon (EMPA 116) at a concentration of 5 $gl^{-1}$ in wash water containing 200 ppm calcium carbonate at a wash temperature of 60° C. for 30 minutes.

The following percentages stain removal were observed:

| | |
|---|---|
| Control | 36% |
| Freshly prepared formulation | 57% |
| Formulation after standing 22 days at 30° C. | 52% |

EXAMPLES 2 AND 3

A 25% by weight suspension was prepared by stirring solid "ESPERASE" protease concentrate (prepared as described in U.S. Pat. No. 3,723,250 at col. 12) into a silicone oil with a viscosity of 1.83 Pascal seconds, which was sold by Diamond-Shamrock under the Trade Mark "NOPCO 8315" silicone defoamer.

The suspension had a viscosity of 7.32 Pascal seconds and was incorporated into build liquid detergents to give the following formulations:

| | Ex. 2 | Ex. 3 |
|---|---|---|
| Sodium dodecyl benzene sulphonate | 6% | 7% |
| Sodium linear $C_{12-18}$ alkyl ether sulphate containing an average of 3 ethyleneoxy units per molecule | 2% | — |
| Coconut diethanolamide | 1.5% | 3% |
| Mixture of mono and di $C_{16-18}$ alkyl phosphate ester | 0.5% | 0.5% |
| Sodium tripolyphosphate | 24% | 24% |
| Sodium carboxymethyl cellulose | 0.1% | 0.1% |
| Enzyme suspension in silicone oil | 1.25% | 1.25% |
| Optical brightening agent | 0.2% | 0.2% |
| Diethylene triamine penta(methylene phosphonate) sodium salt | 0.5% | 0.5% |
| Perfume | 0.3% | 0.3% |
| Water | to 100% | to 100% |
| pH | about 9.0 | about 9.0 |

The protease activity of the formulation of Example 2 was 15.4 kilo Novo protease units (KNPU) per g.

EXAMPLES 4 AND 5

In the same manner as in Examples 2 and 3, a 25% by weight suspension of the "ESPERASE" (Reg. Trade Mark) protease solid concentrate in another silicone antifoam oil having a viscosity of 1.22 Pascal seconds ("BEVALOID" 4237) was prepared and incorporated in the built liquid as in Examples 2 and 3 to give the corresponding formulations Examples 4 and 5 respectively. The suspension had a viscosity of 3.66 Pascal seconds.

The protease activity of the formulation of Example 4 was 14.8 KNPU per g.

STORAGE STABILITY TESTS

The stability of the formuations of Examples 2 and 4 on keeping at 37° C. for 5 weeks were determined and compared to that of a corresponding reference formulation to Example 2 with the same amount of enzyme but no silicone oil.

The residual proteolytic activity of each formulation was determined by the dimethylcasein (DMC) method described in Novo Publication AF 101/4-GB. The results are shown in the following table with activity expressed as a percentage of the initial activity of that formulation:

| Formulation | Residual Activity after time in weeks 2 | 4 | 5 |
|---|---|---|---|
| Example 2 | 80% | 70% | 70% |
| Example 4 | 85% | 65% | 63% |
| Reference | 33% | 9% | n.a. |

EXAMPLES 6 TO 13

A number of alternative protected enzyme systems were each prepared by stirring 25% of solid enzyme concentrate into the hydrophobe and tested as shown in the following Table:

| Example No | Enzyme | Trade Name of Hydrophobe | Chemical Type of Hydrophobe | Viscosity P Sec. of Hydrophobe | Viscosity of system in P. Sec. |
|---|---|---|---|---|---|
| 6 | "TERMAMYL"* | "BEVALOID"* 4237 | Silicone oil + hydrophobic silica | 1.22 | 2.44 |
| 7 | "SAVINASE"* | "BEVALOID"* 4237 | Silicone oil + hydrophobic silica | " | 2.74 |
| 8 | "ALKALASE"* | "BEVALOID"* 4237 | Silicone oil + hydrophobic silica | " | 2.13 |
| 9 | "ALKALASE"* | "WACKER"* S132 + "WACKER"* AK50 | Silicone oil + hydrophobic silica diluted with silicone oil | 9.76 | |
| 10 | "TERMAMYL"* | "WACKER"* S132 + "WACKER"* AK50 | Silicone oil + hydrophobic silica diluted with silicone oil | | 10.06 |
| 11 | "ESPERASE"* | "CATANEX"* 79 | Petroleum bright stock | 1.62 | 4.09 |
| 12 | "ESPERASE"* | "VASELINE"* | Petroleum jelly | | |
| 13 | "ESPERASE"* | "EMPICOL"* 7062P | mixed mono/di $C_{16-18}$ alkyl acid phosphate | | |
| 14 | "ESPERASE"* | "WACKER"* S132 | Silicone oil + hydrophobic silica | 22.7 | |

*Registered Trade Mark

Each of Examples 6 to 14 was used as the enzyme system in a sample of liquid detergent according to Example 3. Each was found to exhibit substantially improved retention of enzyme activity and stain removal compared with unprotected enzyme on storage for two weeks at ambient temperature.

EXAMPLE 15

A dishwashing powder has the following formulation:

| A dishwashing powder has the following formulation | |
|---|---|
| Fatty alcohol 12 mole ethoxylate (Registered Trade Mark "EMPILAN" KCMP 0705/F) | 2% |
| Sodium tripolyphosphate | 30% |

-continued

| A dishwashing powder has the following formulation | |
|---|---|
| Chlorinated trisodium phosphate | 9% |
| Borax | 2% |
| Sodium metasilicate | 8% |
| Example 10 | 0.5% |
| Sodium carbonate | balance |

EXAMPLE 16

A dishwashing liquid has the following formulation:

| A dishwashing liquid has the following formulation | |
|---|---|
| 30% Active aqueous sodium xylene sulphonate (Registered Trade Mark "ELTESOL" SX30) | 10% |
| 80% active aqueous synthetic alcohol 8 mole ethoxylate (Registered Trade Mark "EMPILAN" KA880) | 0.5% |
| Potassium hydroxide | 1% |
| Tetra potassium pyrophosphate | 15% |
| Potassium silicate | 10% |
| Example 9 | 0.5% |
| Water | balance |

EXAMPLE 17

A hard surface cleaner has the folowing formulation:

| A hard surface cleaner has the folowing formulation | |
|---|---|
| 30% sodium xylene sulphonate (Registered Trade Mark "ELTESOL" SX30) | 10% |
| 80% synthetic alcohol 8 mole ethoxylate (Registered Trade Mark "EMPILAN" KA880) | 2% |
| 30% sodium lauryl sulphate (Registered Trade Mark "EMPILAN" SL30) | 5% |
| Tetra potassium pyrophosphate | 5% |
| Example 12 | 0.5% |
| Water | balance |

EXAMPLE 18

A carpet shampoo has the following formulation:

| A carpet shampoo has the following formulation | |
|---|---|
| 14% sodium lauryl sulphate + 14% lauric monoethanolamide sulphosuccinate (Registered Trade mark "EMPIMIN" 3119) | 25.0% |
| Example 8 | 0.5% |
| water | balance |

EXAMPLE 19

A carpet shampoo has the following formulation:

| A carpet shampoo has the following formulation | |
|---|---|
| 28% sodium synthetic lauryl sulphate (Registered Trade Mark "EMPICOL" LX 288/5) | 36% |
| Lauric isopropanolamide | 2% |
| Example 13 | 0.5% |
| Water | balance |

EXAMPLE 20

An oven cleaner has the following formulation:

| An oven cleaner has the following formulation | |
|---|---|
| Nonylphenyl 9 mole ethoxylate (Registered Trade Mark "EMPILAN" NP9) | 15% |
| Propylene glycol | 20% |
| Sodium tripolyphosphate | 10% |
| Example 7 | 0.5% |
| Water | balance |

EXAMPLE 21

An oven cleaner has the following formulation:

| An oven cleaner has the following formulation | |
|---|---|
| 27% lauryl ethersulphate (Registered Trade Mark "EMPIMIN" 27/T | 20% |
| Sodium hydroxide (as solid) | 8% |
| Example 12 | 0.5% |
| Water | balance |

We claim:

1. A protected enzyme system consisting essentially of a hydrophobic fluid which is substantially insoluble in aqueous liquid laundry detergents and a detergent enzyme dispersed in said fluid.

2. A system according to claim 1 wherein said fluid has a viscosity of from 0.05 to 200 Pascal seconds.

3. A system according to claim 2 wherein said fluid has a viscosity of from 0.8 to 100 Pascal seconds.

4. A system according to claim 1 wherein said fluid consists essentially of a silicone oil.

5. A system according to claim 4 wherein said oil additionally contains hydrophobic silica.

6. A system according to claim 2 wherein said fluid is a hydrocarbon.

7. A system according to claim 1 wherein said fluid is petroleum jelly.

8. A protected enzyme system consisting essentially of enzyme containing granules coated with a fluid hydrocarbon.

9. A system according to claim 8 wherein said hydrocarbon is petroleum jelly.

10. A system according to claim 1 wherein said hydrophobic fluid contains dispersed droplets of a solution of said enzyme in a solvent selected from the group consisting of water and water miscible mono-di- and polyhydric alcohols and ether alcohols and mixtures thereof.

11. A system according to claim 1 wherein said hydrophobic fluid contains dispersed particles of a solid enzyme concentrate.

12. A system according to claim 1 wherein the particle size of said dispersed enzyme is from 5$\mu$ to 1 mm.

13. A fluid cleaning composition consisting essentially of water, surfactant and a dispersed detergent enzyme said enzyme being protected from said composition by a hydrophobic fluid which is substantially insoluble in said composition.

14. A cleaning composition according to claim 13 consisting essentially of water, surfactant and a dispersed enzyme system, said enzyme system consisting essentially of said hydrophobic fluid having said enzyme dispersed therein.

15. A cleaning composition according to claim 13 consisting essentially of water, surfactant and dispersed enzyme-containing granules, said granules being coated with said hydrophobic fluid.

16. A cleaning composition according to claim 13 consisting essentially of from 30 to 70% water, from 3 to 30% surfactant, from 5 to 35% builder and a stain removing proportion of said enzyme system dispersed therein.

17. A cleaning composition according to claim 16 wherein said protected enzyme system has a particle size of from 2μ to 2.5 mm.

18. A cleaning composition having dispersed therein a protected enzyme system which system consists essentially of particles of detergent enzyme dispersed in a hydrophobic fluid having a viscosity of from 0.05 to 200 Pascal seconds.

19. A powder detergent composition according to claim 18 consisting essentially of from about 5 to about 30% by weight of surfactant selected from the group consisting of anionic sulphated and sulphonated surfactants, soaps and non-ionic surfactants and mixtures thereof, from about 10 to about 355 by weight of a builder selected from the group consisting of alkalimetal phosphates, condensed phosphates, phosphonates, carbonates, silicates, citrates, nitrilotriacetates, ethylenediaminetetracetates, zeolites and mixtures thereof, from about 15 to about 80% by weight of an inert filler, from 0 to 15% by weight of a peroxy bleach and from 0.01 to 10% by weight of said protected enzyme system.

* * * * *

UNITED STATES PATENT AND TRADEMARK OFFICE
CERTIFICATE OF CORRECTION

PATENT NO. : 4,906,396

DATED : March 6, 1990

INVENTOR(S) : FALHOLT et al

It is certified that error appears in the above-identified patent and that said Letters Patent is hereby corrected as shown below:

In the title page, under "Inventors", insert the following as the fourth inventor of the patent:

Edward Tunstall Messenger
Cumbria, England

Signed and Sealed this

Tenth Day of December, 1991

*Attest:*

HARRY F. MANBECK, JR.

*Attesting Officer* *Commissioner of Patents and Trademarks*